United States Patent [19]

Auchinleck et al.

[11] Patent Number: 4,817,592
[45] Date of Patent: Apr. 4, 1989

[54] TOROIDAL SURGICAL SHIELD

[75] Inventors: Geoffrey F. Auchinleck, Vancouver; James A. McEwen, Richmond; John C. Osborne, Port Coquitlam; Carlo R. Bussani, Burnaby, all of Canada

[73] Assignee: Andronic Devices, Ltd., Vancouver, Canada

[21] Appl. No.: 137,252

[22] Filed: Dec. 22, 1987

Related U.S. Application Data

[63] Continuation-in-part of Ser. No. 6,131, Jan. 23, 1987.

[51] Int. Cl.<sup>4</sup> ................................................ A61F 5/04
[52] U.S. Cl. .................................... 128/855; 206/438; 128/856
[58] Field of Search ...................... 128/132 R, 132 D; 206/438

[56] References Cited

U.S. PATENT DOCUMENTS

| 4,043,328 | 8/1977 | Cawood, Jr. et al. ......... 128/132 D |
| 4,069,913 | 1/1978 | Harrigan ...................... 128/132 R X |
| 4,275,812 | 6/1981 | Poncy et al. ................ 128/132 R X |
| 4,593,699 | 6/1986 | Poncy et al. ......................... 128/660 |
| 4,679,552 | 7/1987 | Caspari ............................. 128/132 D |

Primary Examiner—Francis Jaworski
Attorney, Agent, or Firm—Stoel Rives Boley Jones & Grey

[57] ABSTRACT

Apparatus useful in surgery for holding part of a patient's body such as a limb, portion of a limb, extremity organ or tissue in a number of different positions required by a surgeon for the performance of a surgical procedure, and for establishing a sterile barrier between a surgical site and a patient's limb or body part while the limb or body part is being grasped by a such positioning apparatus.

7 Claims, 10 Drawing Sheets

TOROIDAL SURGICAL SHIELD

REFERENCE TO RELATED APPLICATION

This is a continuation-in-part of U.S. application Ser. No. 006,131 filed Jan. 23, 1987.

FIELD OF THE INVENTION

This invention pertains to apparatus for holding part of a patient's body, such as a limb, portion or a limb, extremity organ or tissue, in a number of different positions required by the surgeon for the performance of a surgical procedure, and pertains to related means for economically and efficiently providing a sterile barrier between the surgical site and the positioning apparatus. In particular the invention pertains to a limb positioning apparatus comprising a plurality of positioning members interconnecting a grasping means for grasping a part of a patient's body, to a supporting point, each member including selectably positionable joints which may be locked in a selected position, and apparatus for establishing a sterile barrier between a surgical site and a patient's limb, while the limb is connected to a supporting point by a limb positioning apparatus, such that the combination of the limb, limb positioning apparatus, the supporting point and the patient's body form an annular shape.

BACKGROUND OF THE INVENTION

Many surgical procedures require that a patient's body part, such as a limb, portion of a limb, extremity, organ or tissue be positioned in a number of different positions for the performance of a surgical procedure. It is desirable that the operating surgeon or surgical assistant be able to move the limb or other body part into other positions and configurations that may be required during the course of the surgical procedure. It is also desirable that any positioning apparatus that may be used to achieve such positions and configurations not obstruct the surgical site, and be able to avoid any obstacles that may exist around the surgical site, such as medical imaging systems, operating room lights, instrument trays, or other apparatus.

Various methods for positioning and supporting a patient's limb or body part are known in the prior art. One common method for positioning a body part is to have a sterile surgical assistant hold the body part in a desired position, and change the position when and as requested by the operating surgeon. This task is fatiguing for the surgical assistant, and this technique may not support the patient's body part in a sufficiently precise and rigid manner for the surgical procedure. Other typical methods for positioning a patient's limb are to rest the limb on a table for that purpose, to hang the limb over part of the operating room table, or to rest the limb on the lap of a seated operating surgeon. All of these techniques offer a very limited range of possible limb configurations, serve to restrict the movement of the surgeon, and result in reduced precision and rigidity of support.

In addition to the methods for positioning illustrated above, apparatus for supporting and positioning body parts exists in the art. One common supporting means consists of slings attached to the patient's limb, ropes and occasionally weights, which are hung over or tied to operating room light fixtures, intravenous fluid support stands, or other operating room fixtures in order to suspend the limb (e.g. see Herschman, Z. J., Frost, E. A. M, Goldiner, P. L.; Pulse Oximetry during Shoulder Arthroscopy, Anesthesiology, 65:565-566, 1986). These types of supporting means are difficult to set up and take down, clumsy to adjust, and often obstruct the surgical site. Furthermore, adjusting such apparatus to achieve a new position may require the assistance of a nonsterile person, in that operating room fixtures and support stands that may require re-positioning are not considered sterile, hence cannot be touched by a surgeon. This may preclude optimal positioning of the limb or body part, as the surgeon may no longer have direct control over the final position of the limb or body part.

Additional specialized positioning devices for supporting limbs or body parts are known in the prior art. One class of positioning device includes a wide variety of devices for holding a patient's leg in position for arthroscopic knee surgery. Such devices generally grip the patient's leg near the foot, and also at the thigh. Means are provided to allow the surgeon to move the lower leg into various configurations suitable for arthroscopic surgery, while the upper part of the leg is held in a fixed position. Such devices are suitable only for surgery at or near the knee, and are not suitable for use during preparation of the limb for surgery. In addition, these devices cannot be positioned so as to avoid obstacles near the surgical site, may obstruct the surgical site, do not offer any means for detaching the grasping means and attaching another grasping means for grasping another body part, and are difficult to drape to establish a sterile barrier between the surgical site and the patient's limb while it is grasped by the positioning device.

In an attempt to overcome the drawbacks of existing devices for holding retraction devices during surgery, the Elmed Company of Addison Illinois manufactures a multijointed mechanism, the "Elmed Retract-Robot", catalog number 15088-00 single arm instrument, which can be locked in a wide range of positions with a thumbscrew arrangement. This device, although not intended for manipulation of all limbs and body parts, could perhaps be adapted with appropriate grasping means to solve some of the problems heretofore described. However, such a device, even if configured with an appropriate grasping means, would still not be suitable for a wide range of surgical procedures, as the device does not provide a sufficiently large range of motion for many such procedures. It is conceivable that several such devices could be connected together to create a larger structure with an increased range of motion, but such a structure would be very difficult to re-position, in that each device in the structure would have to be unlocked, positioned and locked individually each time a new position is required. In addition, it is unlikely that several such devices connected together would offer sufficient strength to support a patient's leg or arm, there is no convenient way for a grasping means to be detached and replaced with another grasping means for grasping a different body part, and the device is difficult to drape to establish a sterile barrier between the surgical site and the patient's limb while the limb is grasped by the positioning device, hence the device would typically be sterilized before each use, which is time consuming and costly.

Also known in the art is a similar retraction device, widely known by surgeons throughout the world as a "Greenberg" brain retractor. This retraction device consists of a plurality of ball and socket joints, threaded upon a length of cable. This cable may be tightened with a lever mechanism to increase the friction between each ball and socket joint. The Greenberg brain retractor is not suitable for manipulation of a wide range of limbs due to its typically small size. In addition, the strength of the ball and socket joints when fully locked is insufficient to support the loads typically expected when positioning a patient's limb, there is no convenient way for a grasping means to be detached and replaced with another grasping means for grasping a different body part, and the device is difficult to drape to establish a sterile barrier between the surgical site and the patient's limb while the limb is grasped by the positioning device, hence the device would typically be sterilized before each use, which is time consuming and costly.

One problem that is common to any means of supporting a patient's limb or body part is that of establishing a suitable sterile barrier between a surgical site and a patient's limb or body part while it is being supported by a positioning means. The patient's limb, the positioning means, the supporting point to which the positioning means is connected, and the patient's body form a closed annular shape. This closed annular shape is usually established when the patient's limb is connected to the positioning means to hold the limb in position for preparation of the surgical site. It is undesirable to detach the patient's limb from the positioning means to apply a sterile surgical drape to the limb or positioning means after the surgical site is prepared, as this may contaminate the prepared surgical site. It is also undesirable to cover the limb and positioning means with sterile drapes before the surgical site is prepared, as the solutions used for preparation may contaminate the drape.

One method of draping such an annular shape is to drape flat sterile sheets over the limb and positioning means, and fasten the drapes in position with sterile clips or tape. This may leave openings in the drape, compromising the integrity of the sterile barrier, and will usually leave a large amount of excess drape hanging from the limb and supporting means, such that it may obstruct the surgical site.

A preferred form of sterile cover for such an annular shape consists of an elongated flexible tube, made of an impervious sterile material such as a flexible thermoplastic, which is placed over the limb and positioning means to act as a sterile sleeve. Such a sleeve may be considered to be a torus, where a torus is defined by the Oxford English Dictionary as "a surface generated by the rotation of a plane closed curve about an axis lying in its plane, but not intersecting it." The draping problem can thus be described as a need to interlink a toroidal sterile drape with a closed annular shape, in which the annular shape, when first closed, is considered to be nonsterile or contaminated.

Although many examples of sterile drapes in the form of a elongated flexible tube or torus are known in the art, none provide a means so that such a sterile drape can be interlinked with a nonsterile or contaminated limb or positioning means without contaminating the drape.

A sterile drape must be packaged so that there is a means by which the sterile drape can be removed from the nonsterile outer package in such a way that the sterile drape is not contaminated. This problem is generally overcome by providing an outer package which can be opened by a nonsterile person to expose the sterile drape such that a sterile person can remove the drape without contaminating it. As the edges of the outer nonsterile package are considered to be contaminated, it is important that some means be provided to keep the edges of the outer package well away from the sterile drape and the hands of the sterile person attempting to remove the drape from the package.

The following U.S. patent application of the applicants is more or less relevant to the subject matter of the applicants' invention.

U.S. application filed Feb. 19, 1986, Continuation-in-part, Ser. No. 831,001; Title: Advanced Medical Robot; Inventors: James Allen McEwen et al.

SUMMARY OF THE INVENTION

The present invention provides apparatus for holding part of a patient's body such as a limb, portion of a limb, extremity, organ or tissue in a number of different positions required by the surgeon for the performance of a surgical procedure, said positioning apparatus consisting of a grasping means, for grasping a part of a patient's body, and a plurality of positioning members connected to a supporting point, each positioning member having selectably positionable joints attached to attaching means for connecting each positioning member to other such members, or to the grasping means or to the supporting point. Each positioning member also includes a locking means for locking the joints in a selected position, an actuating means for locking and unlocking the locking means in response to a control signal, and a signal generating means which may be attached to the positioning member, so that an operator can generate control signals for locking and unlocking either individual positioning members, or predefined groups of positioning members simultaneously.

In another aspect, the invention provides apparatus for establishing a sterile barrier between a sterile surgical site and a patient's limb, while said limb is attached to a supporting point by a limb positioning apparatus, such that the combination of the limb, the limb positioning apparatus, the supporting point and the patient's body for an annular shape.

Another object of the invention is to provide a limb positioning apparatus consisting of a plurality of positioning members, in which said positioning members may be individually re-positioned without having an effect upon the rest of the members making up the apparatus.

Advantageously, the limb positioning apparatus is constructed of identical positioning members, any number of which may be linked together to provide the limb positioning apparatus with a greater or lesser reach or number of degrees of freedom. Furthermore, said positioning members may be of sizes and strengths suitable for manipulating various limbs and body parts.

Other objects of the present invention include: providing a mechanism for attaching and detaching a wide variety of grasping means to the limb positioning apparatus, providing a control signal generating means for locking and unlocking the positioning apparatus which is attached to said positioning apparatus such that an operator must be in contact with the structure to unlock the supporting apparatus, and providing a positioning apparatus that may be largely constructed out of X-ray translucent materials so that the positioning members will minimally interfere with medical X-ray images taken of the body part while it is held by the limb positioning apparatus.

A limb positioning apparatus in accordance with the invention comprises one or more similar positioning members, each positioning member having a cylindrical shape, at each end of which is located a ball joint mechanism providing three mutually perpendicular rotational degrees of freedom to the limb positioning apparatus. Within each positioning member is included means for alternately locking and unlocking said ball joints.

A sterile draping means in accordance with the invention consists of an elongated tube made of a flexible, impervious sterile material, such as a flexible thermoplastic material, rolled or folded into a toroidal shape. This toroidal shape is sealed within a removable impervious material which serves to protect the sterile materials from contamination, and provides a means for exposing the sterile elongated tube without contaminating it. The draping apparatus can be placed around a positioning apparatus before it is attached to a patient's limb, and the removable impervious material removed when appropriate, to allow the sterile elongated tube to unrolled or unfolded over the positioning apparatus and patient's limb to establish a sterile barrier.

DETAILED DESCRIPTION OF THE PREFERRED EMBODIMENT

Figure 1:
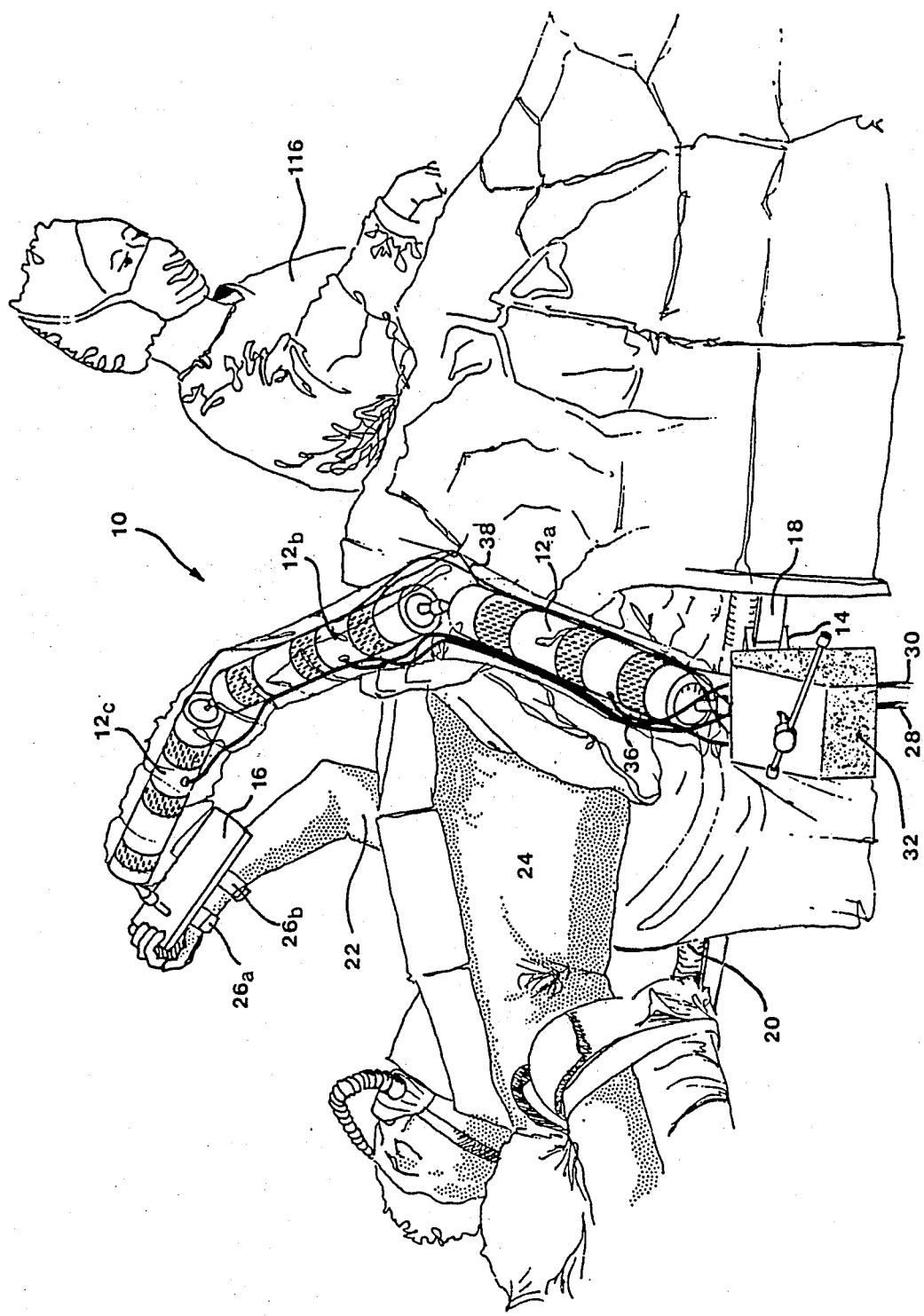
FIG. 1 is a pictorial illustration of a limb positioning apparatus configured as an arm manipulator for assisting in the performance of surgical operations.

FIG. 1 is a pictorial illustration of one possible configuration of limb manipulator 10 according to the invention, as it would be used for supporting a patient's limb for arthroscopic surgery of the shoulder. In this configuration, limb manipulator 10 constitutes three identical positioning members 12a, 12b and 12c, which are connected together, and in turn are connected to table mounting means 14 and grasping means 16. Table mounting means 14 is clamped to side rail 18 of operating-room table 20, so that limb manipulator 10 will move in the same reference frame as the patient's entire body when the patient's entire body is re-positioned by adjusting the height, tilt or orientation of the operating-room table. Grasping means 16 is connected to limb 22 of patient 24 with fastening means 26. Pressurized gas supply hose 28 and electrical power cord 30 are connected to electronics box 32, which is part of table mounting means 14. Protective sheath 34 (not shown in FIG. 1) encloses identical positioning members 12a, 12b, and 12c, gas supply tubes 36 and control wires 38.

Figure 2:
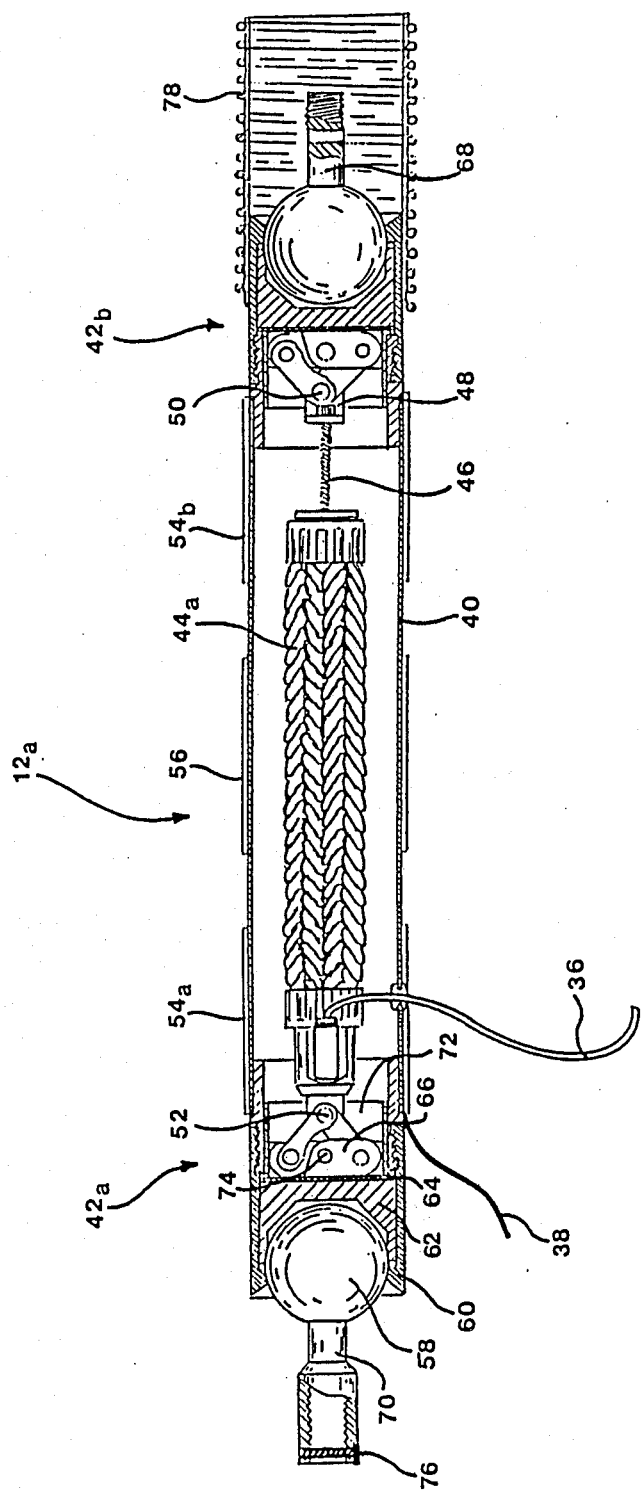
FIG. 2 is a cross section drawing of one positioning member of the limb positioning apparatus of FIG. 1.

A typical positioning member 12a (best seen in FIG. 2) consists of tube 40, at the ends of which are attached a ball joint mechanisms 42a and 42b. Within tube 40 is pneumatic actuator 44a, which in the preferred embodiment is a Bridgestone rubber actuator (Bridgestone Corp., Tokyo, Japan). Connected to pneumatic actuator 44a is gas supply tube 36. One end of pneumatic actuator 44a is connected to a tension adjusting mechanism consisting of screw 46 and coupling 48. Coupling 48 is pivotally connected to one ball joint mechanism 42b via pivot 50. The opposite end of pneumatic actuator 44a is pivotally connected to the other ball joint mechanism 42a via pivot 52. Fastened to the outside surface of tube 40 are three groups of membrane switches 54a, 54b, and 56, connected to control wire 38, the functions of which are hereinafter described.

A typical ball joint mechanism 42a consists of ball 58, ring 60, piston cup 62, pressure plate 64, and lever mechanism 66. Ball 58 is rigidly attached to a positioning member connection means which may consist of either threaded stud 68 or threaded socket 70, and is located within ring 60, which in turn is rigidly attached to tube 40. Also within ring 60 is located piston cup 62, which is free to move along the axis of tube 40 and ring 60 such that piston cup 62 can contact ball 58. Located between the flat side of piston cup 62 and lever mechanism 66 is pressure plate 64, which is preferably made of a hard material such as spring steel. Lever mechanism 66 is pivotally attached to retainer 72 with fixed pivot 74. In the preferred embodiment, lever mechanism 66 consists of four pieces of a hard material such as tool steel pivotally connected in two places to form a scissor mechanism.

In the preferred embodiment, tube 40, ring 60, piston cup 62 and retainer 72 are constructed of aluminum. This material is chosen because it is translucent to X-ray imaging devices, and hence will not obscure images taken through the limb manipulator. Actuator 44a, and membrane switches 54a, 54b, and 56 are transparent to X-ray imaging devices, such that only ball 58, pressure plate 64, lever mechanism 66, screw 46 and coupling 48 will obstruct an X-ray image. The size and location of these components is such that they will minimally obscure an X-ray image.

In operation, the condition of ball joint mechanisms 42a and 42b depend on the condition of pneumatic actuator 44a. As pressurized gas is supplied to pneumatic actuator 44a through gas supply tube 36, pneumatic actuator 44a begins to contract. This contraction motion acts on lever mechanism 66, causing lever mechanism 66 to push on pressure plate 64. Pressure plate 64 pushes upon piston cup 62, causing piston cup 62 to move into contact with ball 58. Ball 58 is therefore pressed firmly into ring 60. The force of contact between ring 60 and ball 58, and piston cup 62 and ball 58, causes an increase in friction forces between these surfaces. This friction force locks ball 58 in position with respect to ring 60 and piston cup 62, preventing rotation of ball 58 about any axis. Ring 60 and piston cup 62 preferably have surfaces that are contoured to fit ball 58 to increase the friction forces and reduce the pressure between these components.

In the preferred embodiment, positioning member 12a may be connected to positioning members 12b and 12c with threaded stud 68, threaded socket 70, locking screw 76, and spring collar 78. Each positioning member 12a, 12b, and 12c, is constructed with a threaded stud similar to threaded stud 68 at one end and threaded socket similar to threaded socket 70 at the other end so that positioning members 12a, 12b and 12c can be freely interchanged. A spring collar similar to spring collar 78, which in the preferred embodiment consists of a short section of reinforced vacuum hose, is fitted between each pair of positioning members. In use, spring collar 78 applies a restoring force to the movable joint formed by ball joint mechanism 42a, such that interconnected positioning members 12a, 12b, and 12c tend to align axially.

Limb manipulator 10, consisting of one or more of positioning members 12a, 12b and 12c connected together, may be connected to grasping means 16 via one of the threaded sockets similar to threaded socket 70 on one of positioning members 12a, 12b or 12c, and secured with a locking screw similar to locking screw 76. Grasping means 16 consists of rigid rectangular plate 80 (best seen in FIG. 5) to which is rigidly fastened threaded stud 126, similar to threaded stud 68, which in use may be connected to threaded socket 70 of positioning member 12a, or the similar threaded socket of positioning members 12b or 12c. Attached to rectangular plate 80 are fastening means 26a and 26b, which in the preferred embodiment consist of two Velcro TM straps. In use, fastening means 26a and 26b are used to rigidly attach patient's limb 22 to grasping means 16.

Figure 5:
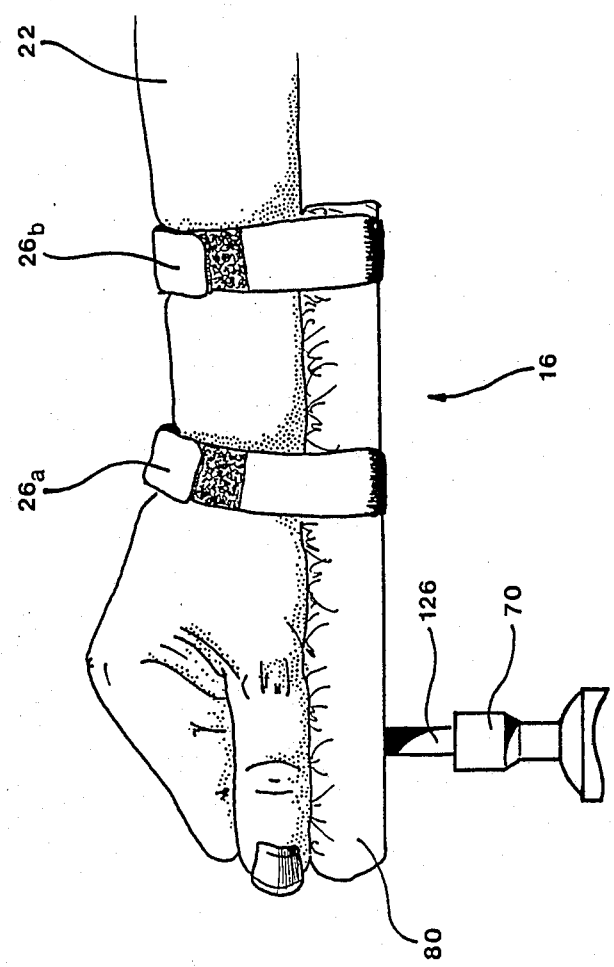
FIG. 5 is a pictorial illustration of the grasping means of the limb positioning apparatus of FIG. 1.

The grasping means shown is FIG. 5 is only one of many possible grasping means that could be used with limb manipulator 10. Grasping means suitable for grasping a patient's foot, upper arm, upper leg, other limb portion, head, organ, tissue or other body part could be connected to limb manipulator 10 in place of grasping means 16 by disconnecting treaded stud 126 from the threaded socket similar to threaded socket 70 on the end of limb manipulator 10 and connecting a different grasping means.

Figure 4:
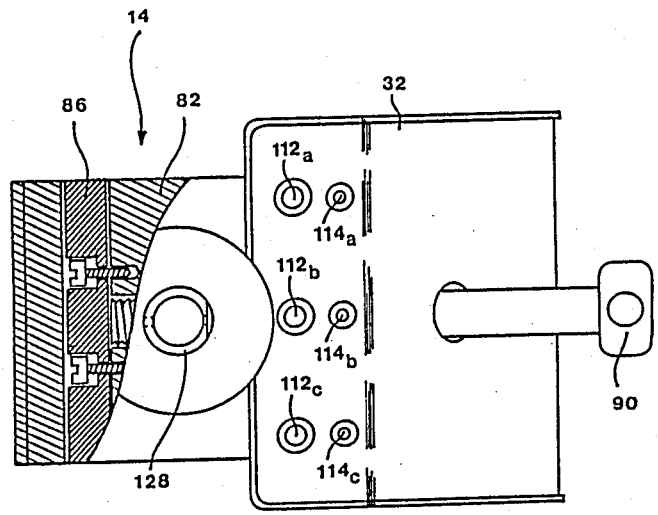
FIG. 4 is a cross section plan view of the apparatus of FIG. 3.
Figure 3:
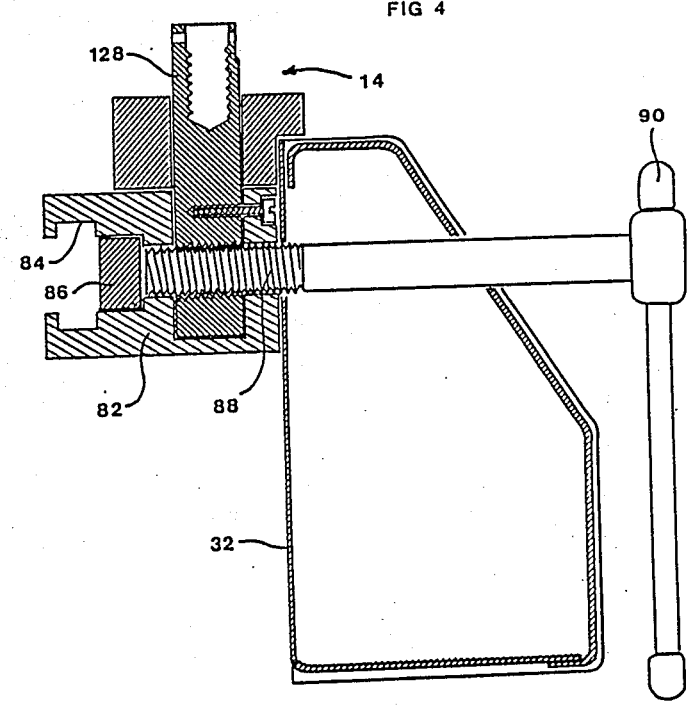
FIG. 3 is a cross section side elevation view of the apparatus for attaching the limb positioning apparatus of FIG. 1 to an operating room table.

Limb manipulator 10 consisting of one or more interconnected positioning members 12a, 12b and 12c may be attached to operating-room table side rail 18 via table mounting means 14 (best seen in FIG. 3 and FIG. 4). Table mounting means 14 consists of mounting block 82, in which is cut channel 84 constructed to fit over side rail 18 of operating-room table 20. Moveably attached to mounting block 82 is pressure bar 86, which is free to move laterally within channel 84. Within mounting block 82 is threaded rod 88, which can come in contact with pressure bar 86. Rigidly attached to mounting block 82 is a threaded socket 128, similar to threaded socket 70, which may be connected to one of positioning members 12a, 12b, or 12c via the threaded stud similar to threaded stud 68 on that positioning member, and locked in place with a locking screw similar to locking screw 76.

In use, mounting block 82 is positioned over table side rail 18 such that table side rail 18 is within channel 84.

Threaded rod 88 can be rotated by the user using handle 90 to cause it to come into contact with pressure bar 86. Pressure bar 86 is thus moved laterally until it is pressed against table side rail 18 to rigidly clamp table side rail 18 between mounting block 82 and pressure bar 86, thereby rigidly fixing table mounting means 14 to operating-room table 20.

Also attached to mounting block 82 is electronics box 32. Within electronics box 32 are power supply 92, valves 94a, 94b, and 94c, and control circuitry 96 (best seen in FIG. 8).

Figure 8:
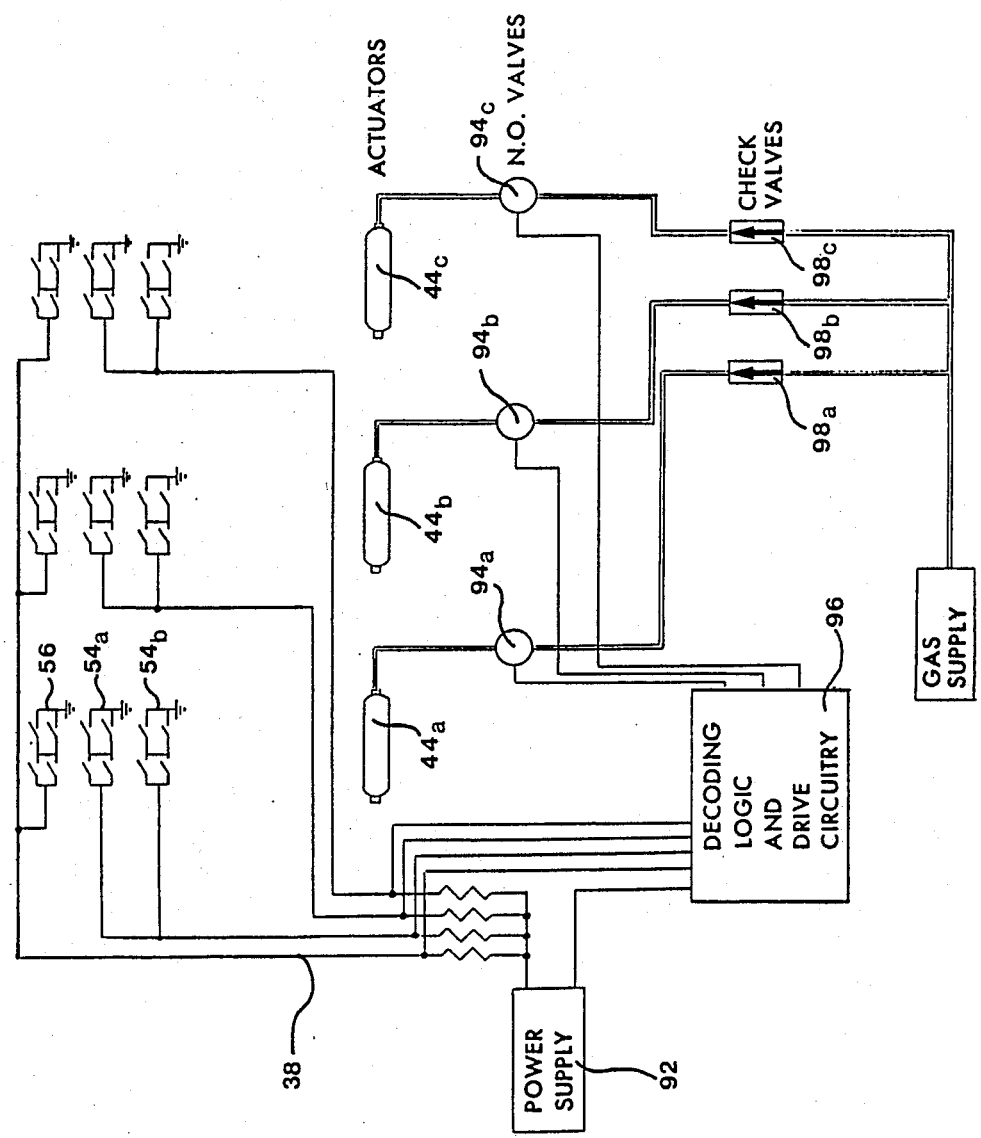
FIG. 8 is a schematic diagram of the electronic and pneumatic circuit of the limb positioning apparatus of FIG. 1.

Membrane switches 54a, 54b and 56 are connected to control circuitry 96 via control wires 38. Membrane switches 54a, 54b and 56 each consist of several active elements connected as shown in FIG. 8. Activating any single active element will not complete the circuit to change the state of any of valves 94a, 94b or 94c. This reduces the risk of accidental activation of valves 94a, 94b or 94c, as two different elements of a membrane switch 54a, 54b or 56 must be activated to operate valves 94a, 94b or 94c. When an appropriate pair of active elements of membrane switches 54a, 54b or 56 are activated, control circuitry 96 causes one or all of valves 94a, 94b or 94c to activate.

Membrane switches 54a and 54b, located near each end of positioning member 12a activate only valve 94a. Valve 94a, when activated cuts off the supply of pressurized gas to actuator 44a within positioning member 12a, upon which membrane switches 54a and 54b are located. In this way, membrane switches 54a and 54b control the flow of pressurized gas to only positioning member 12a, allowing the user to lock and unlock the ball joint mechanisms 42a and 42b of positioning member 12a without affecting the state of positioning members 12b or 12c. Membrane switches similar to membrane switches 54a and 54b are located on positioning members 12b and 12c, to perform a similar function.

Membrane switch 56, located near the center of positioning member 12a, activates all three of valves 94a, 94b and 94c. In this way, membrane switch 56 controls the flow of pressurized gas to all three positioning members 12a, 12b and 12c, allowing the user to lock and unlock the ball joint mechanisms of all three positioning members simultaneously. Membrane switches similar to membrane switch 56 are located on positioning members 12b and 12c to perform a similar function.

In the preferred embodiment, membrane switches similar to membrane switches 54a, 54b and 56 are located on each positioning member of limb manipulator 10. If such a location is not convenient, these membrane switches may be replaced with other means for activating valves 94a, 94b, and 94c. These other activating means may consist of footswitches, sterile hand controls, or other switching means operated by a non-sterile surgical assistant. The membrane switches described could also be located in convenient places other than on limb manipulator 10, such that each positioning member of limb manipulator 10 could be locked and unlocked from a remote location.

In the preferred embodiment, valves 94a, 94b and 94c are SMC NZ3245 normally open pilot operated valves (SMC Pneumatic Inc., Indianapolis Indiana, U.S.A.). Normally open valves are used so that pressurized gas is delivered to actuators 44a, 44b and 44c in each positioning member 12a, 12b and 12c when valves 94a, 94b and 94c are not activated, which causes the ball joint mechanisms of each positioning member 12a, 12b and 12c to lock. In this way, loss of electrical power to control circuitry 96 will not cause the ball joint mechanisms within positioning members 12a, 12b or 12c to unlock.

Pneumatic check valves 98a, 98b and 98c, which in the preferred embodiment are Clippard MCV-1 check valves (Clippard Instrument Laboratory, Inc., Cincinnati, Ohio, U.S.A.), serve a similar function in that they serve to maintain pressure in pneumatic actuators 44a, 44b and 44c within positioning members 12a, 12b and 12c in the event that gas pressure in gas supply hose 28 drops below an acceptable level.

In use, it may be desirable to establish a sterile barrier between limb manipulator 10 consisting of positioning members 12a, 12b and 12c, grasping means 16, and table mounting means 14, and the surgical site. A suitable apparatus for establishing such a sterile barrier consists of elongated flexible tube 100 constructed of a flexible thermoplastic material which may be sterilized, rolled on to rigid tube 102 (best seen in FIG. 6).

Figure 7:
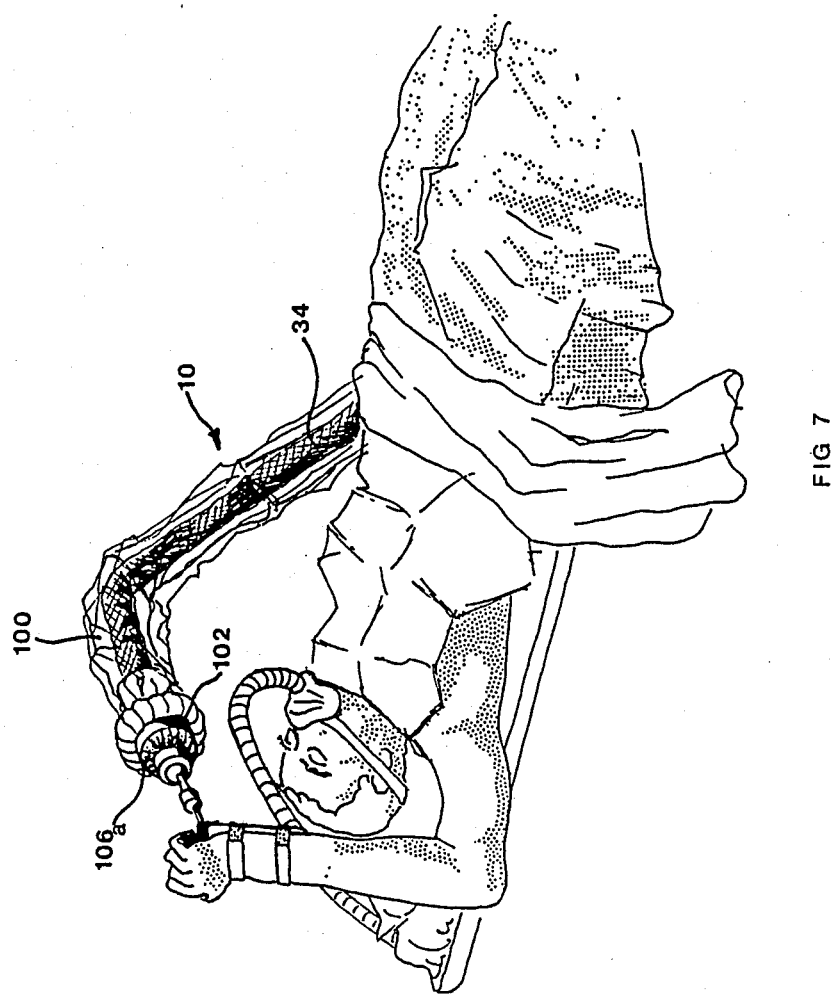
FIG. 7 is a pictorial illustration of the sterile drape of FIG. 6 during application.

Rigid tube 102 is chosen to be of smaller diameter than that of elongated flexible tube 100 so that elongated flexible tube 100, when rolled, fits easily over rigid tube 102. Elongated flexible tube 100 is attached to the outside of rigid tube 102 with seal 104, which may be located near the mid-point of the length of elongated flexible tube 100. Elongated flexible tube 100 may then be rolled up from each end and fitted around rigid tube 102. Attached across each end of rigid tube 102 ar elastic seals 106a and 106b, each consisting of a sheet of elastic material in which are cut holes 108a or 108b. In use, limb manipulator 10 or patient's limb 22 is inserted through holes 108a and 108b. Elastic seals 106a and 106b are thus deformed, and seal tightly against limb 22 or limb manipulator 10, serving to hold rigid tube 102 in position (best seen in FIG. 7).

Elongated flexible tube 100 is covered with sterile wrap 110 which is attached to rigid tube 102 at each end. Sterile wrap 110 is constructed so as to be removable during use as hereinafter described.

Figure 6:
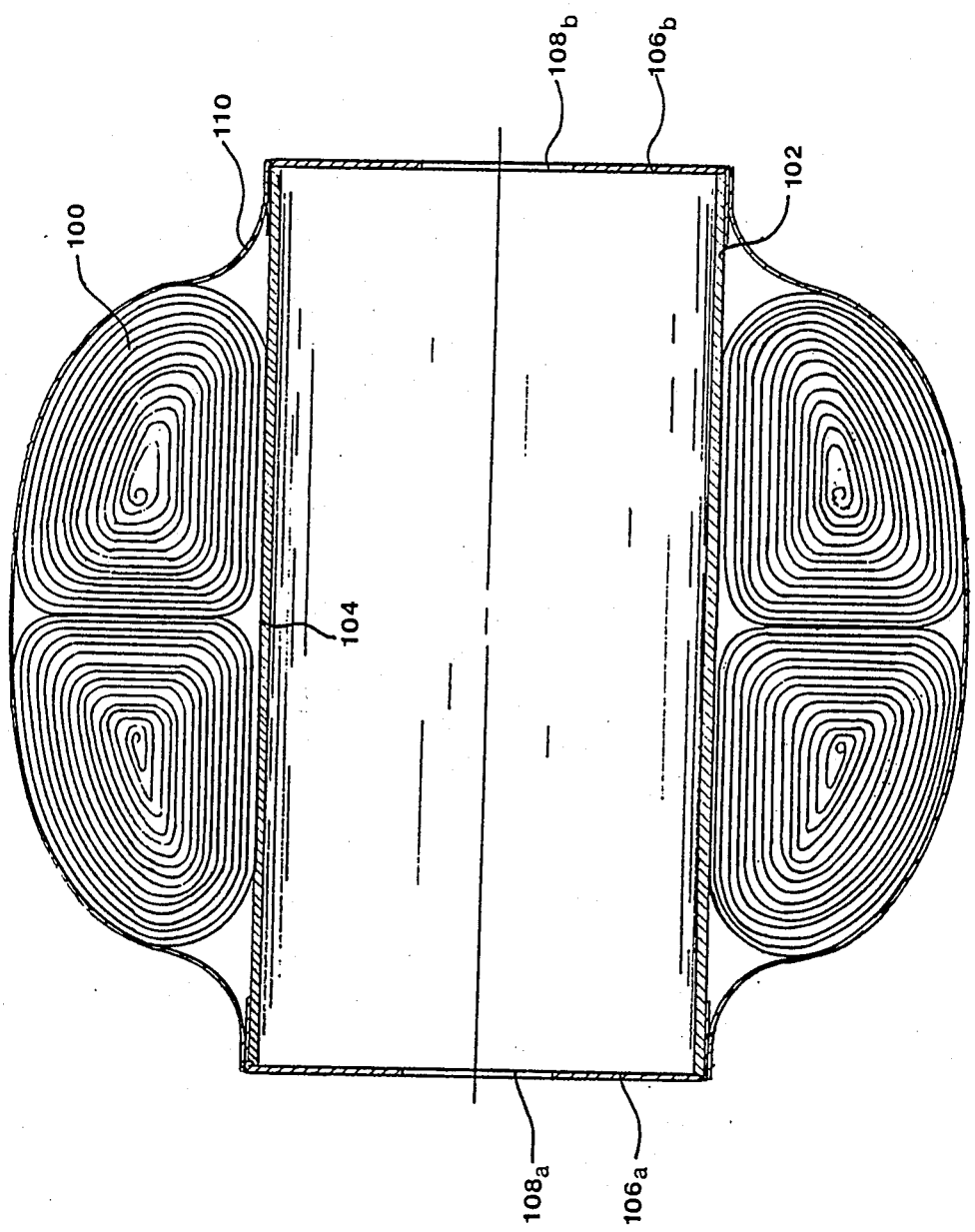
FIG. 6 is a cross section drawing of apparatus for packaging and applying a sterile drape to the limb positioning apparatus of FIG. 1.
Figure 10:
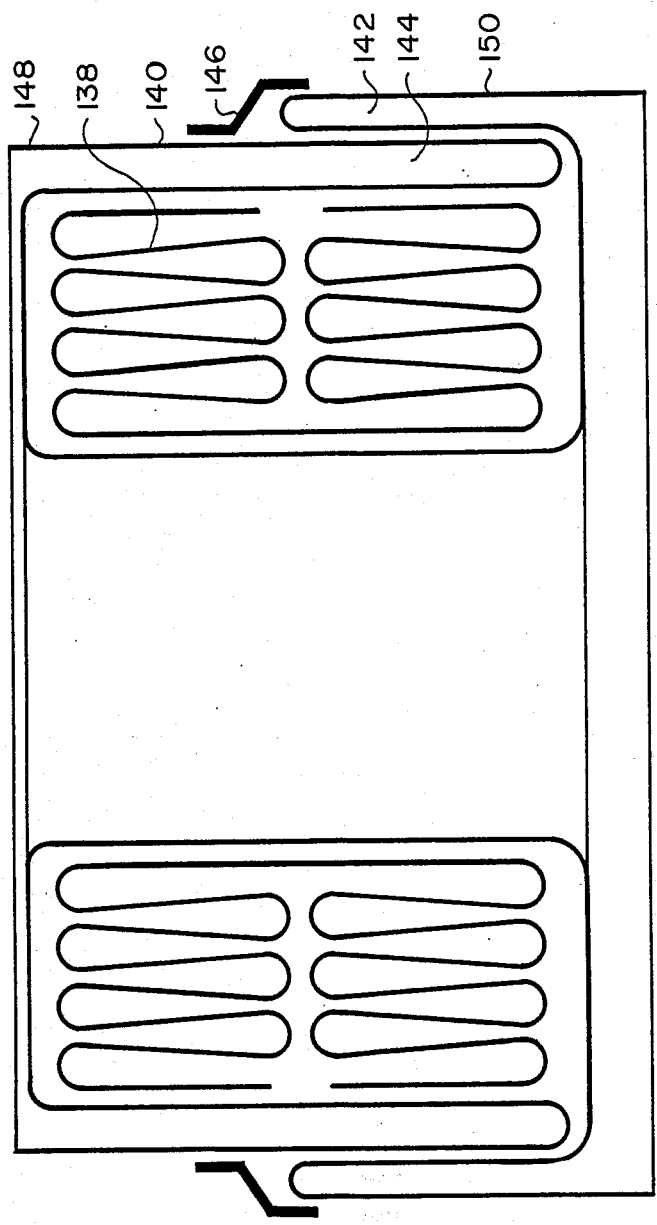
FIG. 10 is a cross section drawing of an alternate embodiment of the draping apparatus of FIG. 6.

An alternative embodiment of the draping apparatus of FIG. 6 is shown in FIG. 10. In this embodiment elongated flexible tube 138, which is constructed of a flexible thermoplastic material which may be sterilized, is multiply folded from both ends to form a double torus. Outer wrap 140 is in the form of a second elongated flexible tube. Outer wrap 140 is passed through the opening in elongated flexible tube 138, and each end is folded back over the outside of elongated flexible tube 138, reversed, and folded back again such that two overlapping cuffs 142 and 144 are formed. Cuffs 142 and 144 are sealed together with removable seal 146 to form a package that totally encloses elongated flexible tube 138 while retaining the toroidal shape. In use, limb manipulator 10 or patient's limb 22 is inserted through the opening in the draping apparatus. Outer wrap 140 is removed during use to expose sterile elongated flexible tube 138, as hereinafter described.

OPERATION BY SURGICAL STAFF

Before use in a surgical procedure, a user must decide how many of positioning members 12a, 12b, and 12c are required to provide sufficient range of motion for the surgical procedure to be performed. A sufficient number of these positioning members (typically 3) are connected together as previously described. Table mounting means 14 is attached to one end of the assembly of positioning members 12a, 12b and 12c, as previously described. Protective sheath 34 may then be fitted over positioning members 12a, 12b and 12c (best seen in FIG. 7). Grasping means 16 is then attached to the other end of the assembly of positioning members 12a, 12b and 12c as previously described.

Before use, gas supply tube 36 from module 12a, and similar gas supply tubes from each of positioning members 12b and 12c are connected to gas outlet connections 112a, 112b and 112c, located on electronics box 32 (best seen in FIG. 4). Similarly, control wires 38 from positioning member 12a, and similar control wires from each of positioning members 12b and 12c are connected to control wire connections 114a, 114b and 114c, also located on electronics box 32.

As shown in FIG. 1, patient 24 is positioned on operating-room table 20 in a normal position for the surgery to be performed, and anesthetized in accordance with standard medical procedures.

Limb manipulator 10 is attached to a convenient place on operating-room table 20 by fitting operating-room table side rail 18 into channel 84 cut into mounting block 82 and turning threaded rod 88 with handle 90 until pressure bar 86 is firmly clamped against operating-room table side rail 18.

The draping apparatus is installed by fitting rigid tube 102 over limb manipulator 10, and sliding it along limb manipulator 10 to a convenient location. Elastic seals 106a and 106b serve to hold rigid tube 102 at this location. Limb manipulator 10 is located in an appropriate orientation for attaching patient's limb 22 to grasping means 16, and patient's limb 22 is then attached to grasping means 16 by tightly wrapping fastening means 26a and 26b about limb 22. Patient's limb 22 is then prepared for surgery in accordance with standard operating room procedures. Rigid tube 102 is then slid along limb manipulator 10 until it is located near the highest point of either patient's limb 22 or limb manipulator 10 (best seen in FIG. 7). Sterile wrap 110 is removed to expose sterile elongated flexible tube 100. Sterile elongated flexible tube 100 is then unrolled over limb manipulator 10 and patient's limb 22.

Figure 11A:
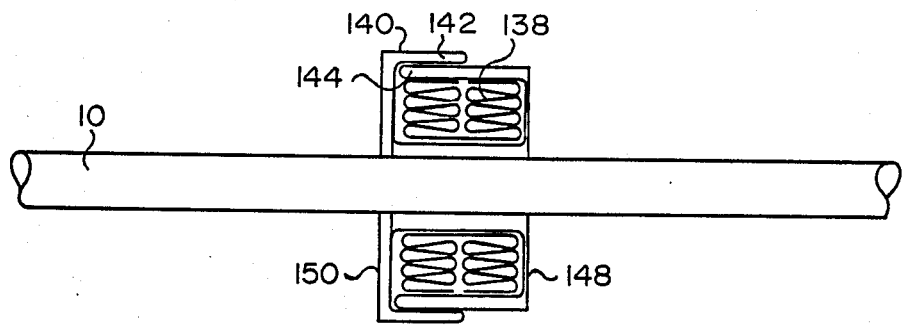
FIG. 11A is a cross section drawing of the alternate draping apparatus of FIG. 10 with the sealing strip removed.
Figure 11B:
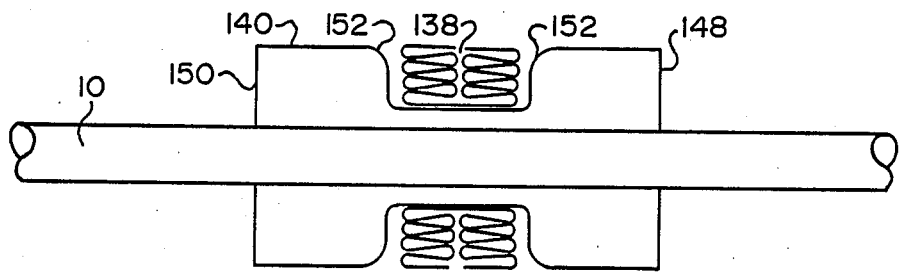
FIG. 11B is a cross section drawing of the alternate draping apparatus of FIG. 10 with the outer protective layer opened to expose the sterile elongated tube.
Figure 11C:
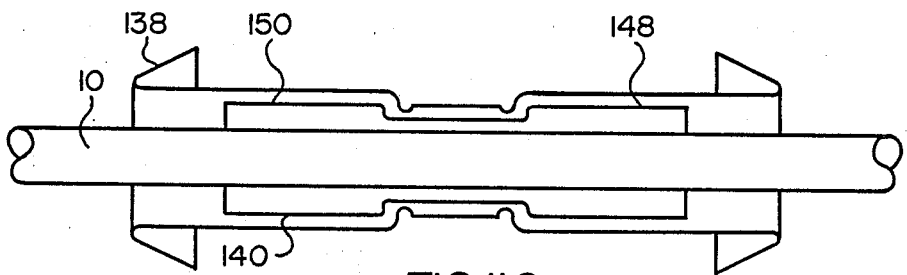
FIG. 11C is a cross section drawing of the alternate draping apparatus of FIG. 10 with the sterile drape unfolded to establish a sterile barrier.

If the alternate draping apparatus of FIG. 10 is used, it is installed by fitting limb manipulator 10 through the opening in the draping apparatus, and sliding the draping apparatus along limb manipulator 10 to a convenient location. Limb manipulator 10 is located in an appropriate orientation for attaching patient's limb 22 to grasping means 16, and patient's limb 22 is then attached to grasping means 16 by tightly wrapping fastening means 26a and 26b about limb 22. Patient's limb 22 is then prepared for surgery in accordance with standard operating room procedures. The draping apparatus is then slid along limb manipulator 10 until it is located near the highest point of either patient's limb 22 or limb manipulator 10. Seal 146 is then removed by a nonsterile person (best seen in FIG. 11A). The nonsterile person then grasps nonsterile tails 148 and 150 of cuffs 142 and 144, and pulls them away from each other, to expose sterile elongated tube 138, which is left resting on sterile inner surface 152 of outer wrap 140, located well away from nonsterile tails 148 and 150 of outer wrap 140 (best seen in FIG. 11B). A sterile person can now unfold sterile elongated tube 138 over limb manipulator 10, patient's limb 22, and outer wrap 140 (best seen in FIG. 11C).

In use, operating surgeon 116 may desire to change the position of limb 22 or limb manipulator 10. If the desired change in position is small, operating surgeon 116 may choose to move only one of positioning members 12a, 12b or 12c of limb manipulator 10. To do this, operating surgeon 116 grasps the positioning member that he wishes to move near one end. This grasping action activates a membrane switch similar to membrane switch 54a or 54b, which in turn activates one of valves 94a, 94b or 94c, causing the pneumatic actuator located within the grasped positioning member to de-activate. When the pneumatic actuator has deactivated, both ball joint mechanisms located within the grasped positioning member unlock. Operating surgeon 116 may now re-position patient's limb 22 and the grasped positioning member. When a new desired position is reached, operating surgeon 116 unlocks his grasp, de-activating the membrane switch, which de-activates the appropriate valve, causing the pneumatic actuator within the previously grasped positioning member to activate, thereby locking both of the ball joint mechanisms located within the previously grasped positioning member.

If the desired change in position is large, operating surgeon 116 may choose to move all the positioning members 12a, 12b and 12c of limb manipulator 10. To do this, operating surgeon 116 grasps any positioning member near its mid-point. This grasping action activates a membrane switch similar to membrane switch 56, which in turn activates all valves 94a, 94b and 94c, causing all the pneumatic actuators located within positioning members 12a, 12b and 12c to deactivate. When the pneumatic actuators have de-activated, all the ball joint mechanisms located within positioning members 12a, 12b and 12c unlock. Operating surgeon 116 may now re-position the patient's limb and all of the positioning members 12a, 12b and 12c. When a new desired position is reached, operating surgeon 116 unlocks his grasp, deactivating the membrane switch, which de-activates all valves 94a, 94b and 94c, causing all the pneumatic actuators within positioning members 12a, 12b and 12c to activate, thereby locking all of the ball joint mechanisms.

When the surgical procedure is complete, sterile elongated flexible tube 100 is cut away and discarded and fastening means 26a and 26b are undone to release patient's limb 22 from grasping means 16. Table mounting means 14 is then removed from table side rail 18 by undoing threaded rod 88. Limb manipulator 10 is then removed to storage.

Many alterations and adaptations may be made to the preferred embodiment described herein. Accordingly the invention is to be limited only by reference to the appended claims. For example, although the preferred embodiment herein described consists of three identical positioning members, more or fewer identical positioning members could be used for increased functional capability. Also, the pneumatic actuators used in the preferred embodiment could be replaced with other pneumatic, hydraulic, or electric actuators to achieve a similar function. The positioning apparatus could also be equipped with a variety of grasping means designed to attach to or support a wide variety of limbs or body parts. The positioning apparatus may also be used as a device for positioning a wide variety of therapeutic or diagnostic apparatus, such as surgical retractors, arthroscopy cameras, suction catheters, mechanisms for applying traction, or other tools or apparatus which must be positioned near the surgical site.

Figure 9:
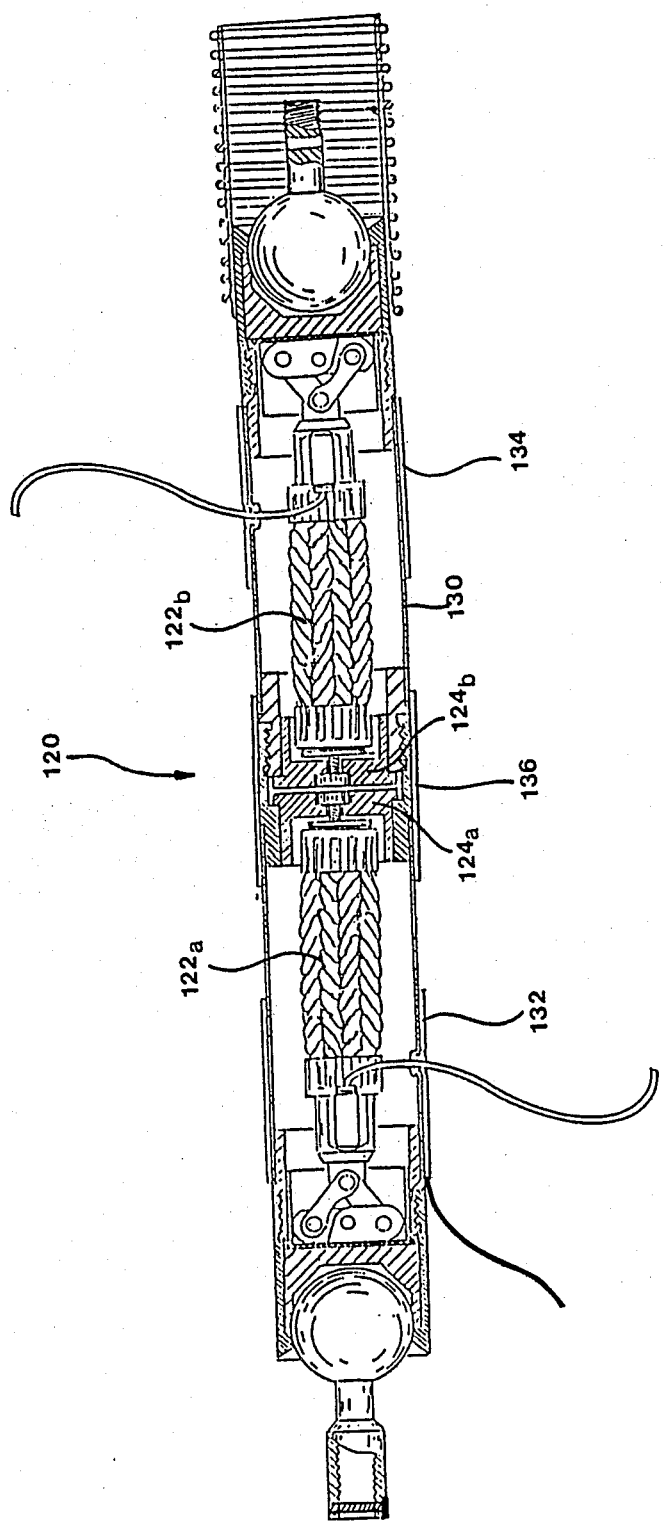
FIG. 9 is a cross section drawing of an alternate embodiment of the positioning member of FIG. 2.

The typical positioning member 12a herein described could also be modified to provide independent locking and unlocking of either ball joint mechanisms 42a or 42b included within a modified positioning member 120, as shown in FIG. 9. In such a modified positioning member 120, actuator 44a is replaced with two pneumatic actuators 122a and 122b, of which one end of each is rigidly attached to retaining blocks 124a and 124b respectively, which in turn is rigidly fixed to the inside of tube 130. In use, such a modified positioning member 120 would be connected to two valves similar to valve 94a, such that either ball joint mechanism could be unlocked independently. Attached to the outside of modified positioning member 120 near each end are membrane switches 132 and 134. Activating one of switches 132 or 134 will cause the ball joint mechanism at that end of modified positioning member 120 to unlock. Near the center of modified positioning member 120 is attached membrane switch 136, which has a function similar to membrane switch 56 of the unmodified positioning member 12a.

The membrane switches 54a, 54b and 56 herein described could be replaced with a number of different switching mechanisms, including footswitches, voice control devices, or remote control pendants. Other types of electrical switches could be mounted on the outer surface of the positioning members as well.

The apparatus herein described for applying a toroidal drape to a closed annular structure could also be used, with some modification, for a wide variety of sterile draping applications. For example, in any surgical procedure in which a limb or body part is to be supported with a structure fastened to the operating-room table or some other fixed support, the sterile draping apparatus described could be used to establish a sterile barrier between the limb or body part and the sterile surgical site. This could include a patient's leg supported by a traditional arthroscopic leg holder, a patient's arm resting upon a supporting table, or a patient's limb held in a traction apparatus.

We claim:

1. Apparatus for forming a sterile barrier around a body part or the like, comprising:
    (a) an elongated tube of sterile flexible material, gathered together into a toroidal shape; and
    (b) removable impervious material enclosing the toroidal shaped tube such that the body part can be passed through the tube while the tube is enclosed by the removable impervious material.

2. Apparatus as defined in claim 1 wherein the elongated tube of sterile flexible material is gathered together by rolling the elongated tube.

3. Apparatus as defined in claim 1 wherein the elongated tube of sterile flexible material is gathered together by folding the elongated tube.

4. Apparatus as defined in claim 1 wherein the elongated tube is gathered together upon a rigid tubular member such that the toroidal shape of the gathered together elongated tube is maintained while the gathered together elongated tube is located on the body part.

5. Apparatus as defined in claim 1 further including elastic means for securing the elongated tube at a selected location along the length of the body part.

6. Apparatus for establishing a sterile barrier between a surgical site and a patient's limb or body part and a positioning apparatus, while said limb or body part is connected to a supporting point by a said positioning apparatus, such that the combination of said limb or body part, said supporting point, said positioning apparatus and the patient's body form a closed annular shape, comprising:

(a) an elongated tube of sterile flexible material, gathered together from both ends so as to form a double toroid, such that said double toroid can be located at any position on said limb or body part of said positioning apparatus; and (b) removable impervious material sealed around said double toroid such that said limb or body part or said positioning apparatus can be passed through said elongated tube without coming into contact with said elongated tube, and such that said impervious material can be removed and said elongated tube can be extended onto said limb or body part and said positioning apparatus in opposite directions.

7. Apparatus for establishing a sterile barrier between a surgical site and a patient's limb or body part and a positioning apparatus, while said limb or body part is connected to a supporting point by said positioning apparatus, such that the combination of said limb or body part, said supporting point, said positioning apparatus and the patient's body form a closed annular shape, comprising:

(a) elongated tube of sterile flexible material, gathered together into a toroidal shape; and (b) removable impervious material sealed around said toroidal shape such that said limb or body part or said positioning apparatus can be passed through said elongated tube, and such that said impervious material can be removed and said elongated tube can be extended onto said limb or body part and said positioning apparatus after they have been connected together to form said annular shape, such that a sterile barrier is formed, and wherein said removable impervious material comprises a second elongated tube which is passed through the opening in said toroidal shape and wherein the ends of said second elongated tube are each in turn folded over the outer surface of said toroidal shape and folded back, so as to form two overlapped cuffs, and wherein said overlapped cuffs are detachably sealed together.

* * * * *